(12) United States Patent
Merlau et al.

(10) Patent No.: US 7,651,693 B2
(45) Date of Patent: Jan. 26, 2010

(54) DURABLE HOLD HAIR STYLING COMPOSITIONS AND METHOD OF USE

(75) Inventors: Melissa Lee Merlau, Elkins Park, PA (US); Alan Isamu Nakatani, Lansdale, PA (US); Curtis Schwartz, Ambler, PA (US); Fanwen Zeng, Belle Mead, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 673 days.

(21) Appl. No.: 10/702,361

(22) Filed: Nov. 6, 2003

(65) Prior Publication Data

US 2004/0096474 A1    May 20, 2004

Related U.S. Application Data

(60) Provisional application No. 60/427,274, filed on Nov. 18, 2002.

(51) Int. Cl.
*A61K 8/02* (2006.01)
(52) U.S. Cl. .................................................. 424/401
(58) Field of Classification Search ................. 424/401
See application file for complete search history.

(56) References Cited

U.S. PATENT DOCUMENTS

| | | | |
|---|---|---|---|
| 3,245,932 A | 4/1966 | Glavis et al. | |
| 3,453,245 A | 7/1969 | Glavis et al. | |
| 4,196,190 A | 4/1980 | Gehman et al. | |
| 4,445,402 A | 5/1984 | Farr et al. | |
| 5,164,177 A | 11/1992 | Bhatt et al. | |
| 6,001,338 A | 12/1999 | Mondet | |
| 6,136,884 A * | 10/2000 | Chen et al. | 523/105 |
| 6,153,206 A * | 11/2000 | Anton et al. | 424/401 |
| 6,165,457 A * | 12/2000 | Midha et al. | 424/78.17 |
| 6,214,328 B1 | 4/2001 | Chang et al. | |
| 6,638,992 B1 * | 10/2003 | Chen et al. | 523/105 |
| 6,805,872 B2 | 10/2004 | Mougin | |
| 2003/0147833 A1 * | 8/2003 | Rollat et al. | 424/70.16 |
| 2004/0057923 A9 * | 3/2004 | Rollat et al. | 424/70.16 |

FOREIGN PATENT DOCUMENTS

| | | |
|---|---|---|
| DE | 22 63 495 | 7/1974 |
| EP | 0 392 767 | 10/1990 |
| EP | 0 619 111 | 12/1996 |
| EP | 0 859 804 | 8/1998 |
| EP | 0 985 405 | 3/2000 |
| GB | 1356395 | 6/1974 |
| JP | 103513/92 * | 4/1992 |
| JP | 2001089325 A | 4/2001 |
| JP | 2002517427 A | 6/2002 |
| WO | WO 99/63955 * | 11/1999 |
| WO | WO 99/63955 | 12/1999 |
| WO | WO 01/96429 | 12/2001 |

OTHER PUBLICATIONS

Nikko Chemcials K.K., "A Handbook of Cosmetic", Nov. 1, 1996, pp. 121-122.

* cited by examiner

*Primary Examiner*—M P Woodward
*Assistant Examiner*—Bethany Barham
(74) *Attorney, Agent, or Firm*—Thomas D. Rogerson

(57) ABSTRACT

The present invention relates to improved hair styling compositions and methods of using such compositions. More particularly, the present invention relates to hair styling compositions with improved durability performance of the hair fixative resins, including resistance to high humidity, low tackiness, and good hold.

2 Claims, No Drawings

DURABLE HOLD HAIR STYLING COMPOSITIONS AND METHOD OF USE

CROSS REFERENCE TO RELATED PATENT APPLICATIONS

This is a non-provisional application of prior U.S. provisional application Ser. No. 60/427,274 filed Nov. 18, 2002.

The present invention relates to improved hair styling compositions and methods of using such compositions. More particularly, the present invention relates to hair styling compositions with improved durability performance of the hair fixative resins, while maintaining resistance to high humidity, low tackiness, and good hold.

Hair styling compositions, such as hair sprays, styling gels, spray gels and mousses are used on hair to hold the hair in a particular shape or configuration. Such compositions typically contain various polymeric resins, gums, and adhesive agents designed to impart desirable properties to the compositions and, ultimately, to hair upon which the compositions are applied. The polymers are used for a variety of purposes including, for example, hair holding, improving volume, and imparting desirable feel properties. Much of the ability of hair styling compositions to hold the hair in a particular shape results from the polymers used in the compositions. The polymers, when applied, form a thin film or weld of polymer on the hair, in the seam between adjacent hair fibers or at a point where the fibers cross one another, and, as a result, hold the hair in a particular shape or configuration.

In order for a polymer to be suitable in a hair styling composition it must exhibit a combination of desirable performance attributes including, for example, compatibility of the polymer with other components of the composition, satisfactory high humidity curl retention, satisfactory stiffness on the hair, low tackiness on the hair, short dry times, no visible residue on the hair, easy shampoo removability, and, for hair spray compositions, easy sprayability resulting in a uniform mist of spray delivered to the hair. In order to impart good hold that has resistance to high humidity and at the same time maintain consumer-desirable properties such as low tackiness, polymers with high glass transition temperatures ("Tg") are typically used. Such high Tg polymers have the drawback that they form films that are extremely hard and brittle. When mechanical stresses, like wind, movement, or touch, are applied to the hairstyle, the stress is transferred to the polymer welds causing them to break. Failure of the welds results in loss of the hairstyle. U.S. Pat. No. 6,214,328 provides examples of improved hair styling compositions comprising acrylic polymers which impart a stiff feel to the hair.

Lower Tg polymers have the benefit that they are not brittle so they do not fracture when stressed. However, low Tg polymers form films which typically are tacky and lack toughness. When applied to the hair, they do not give good holding power or high humidity resistance and have a poor, tacky feel.

Many attempts have been made to develop polymer compositions which would provide the advantages of improved durability and good hold and at the same time maintain consumer-desirable properties such as low tackiness. International Patent Application No. PCT/US00/17161 (Publication No. WO 01/96429) discloses film forming branched/block copolymers wherein the components have different hydrophobicities and different Tg's. U.S. Pat. No. 6,165,457 discloses grafted polymers useful to provide hair spray products with improved properties. The compositions disclosed in these patents each attempt to blend the advantages described above by manipulating the Tg's of the polymer by incorporating into the polymer blocks or grafts made utilizing different monomers to give a polymer with distinct regions having differing properties. In effect, the attempt is to create a single polymer with high Tg regions and low Tg regions. However, the disadvantage of these approaches is that it is necessary to prepare a single polymer with two different regions with differing properties.

We have discovered a polymer composition comprising two individual polymers which provides flexibility and durability to a hair style while retaining other beneficial hair fixative properties, particularly low tackiness. The present invention provides a polymer composition comprising:

a) a first polymer or polymer mixture with a glass transition temperature ("Tg") from 30° C. to 250° C.;

b) a second polymer or polymer mixture with a Tg from minus 20° C. to 35° C.; and c) one or more cosmetically acceptable solvents;

wherein the difference in the Tg's of the first polymer or polymer mixture and the second polymer or polymer mixture is 10° C. or more; and wherein when the first polymer or polymer mixture and the second polymer or polymer mixture are dissolved together in a cosmetically acceptable solvent, which may be the same as or different than the solvent in c), and then dried to form a film, the film has a tensile storage modulus at 20° C. of from $1 \times 10^{10}$ Pascal to $1 \times 10^8$ Pascal and a storage modulus at 70° C. of from $1 \times 10^9$ Pascal to $1 \times 10^6$ Pascal.

When dried, the polymer compositions of this invention provide non-tacky flexible, tough, elastic films wherein the films have a yield stress, below which they display elastic behavior and above which they display ductile behavior.

As a result, hair styling compositions incorporating the compositions of the present invention, when applied to hair, impart a more durable hold and hair style recovery after stress than hair styling compositions which incorporate high Tg polymers and yet avoid the disadvantages typically ascribed to low Tg polymers. Furthermore by varying the Tg's and other properties of the polymers used in the composition, the firmness and flexibility of the hold can also be varied.

For purposes of this invention, the term "first polymer" and "second polymer" each independently include mixtures of polymers.

Unless otherwise specified, the term "hair styling composition" means a pump or aerosol hair spray, styling gel, styling glaze, spray foam, styling cream, styling wax, styling lotion, liquid foam, spray gel, pomade, blow-dry lotion, curl activator, or mousse that is used on hair to hold the hair in a particular shape or configuration. Preferably, the hair styling composition in the present invention is a hair spray. The term "hair" means natural human hair, animal hair, artificial hair, and wigs or hairpieces comprising hair.

As used herein, all percentages are percent by weight, unless otherwise specified. All percentage ranges are inclusive and combinable. All ratios are by weight and all ratio ranges are inclusive and combinable.

Preferably the Tg of the first polymer is from 40° C. to 150° C., more preferably 75° C. to 130° C., most preferably 75° C. to 100° C. Preferably the Tg of the second polymer is from 0° C. to 35° C., more preferably 5° C. to 30° C., even more preferably 15° C. to 30° C., and most preferably 20° C. to 30° C. Preferably the difference in Tg between the first and second polymers is 20° C. or more, more preferably 30° C. or more. Preferably the ratio of the first polymer to the second polymer in the composition is from 99:1 to 10:90, more preferably 20:80 to 80:20, most preferably 35:65 to 65:35.

The first and second polymers are each independently selected from block, graft, and branched homopolymers and copolymers derived from one or more ethylenically unsaturated monomers, polyurethanes, polyureas, polyesters, polyesteramides, condensation polymers, and mixtures thereof. The ethylenically unsaturated monomers and the polyurethane, polyurea, polyester and polyesteramide components are preferably selected to provide the desired properties in the resulting polymer compositions.

Preferably the ethylenically unsaturated monomers are independently selected from methacrylic acid; acrylic acid; methacrylate esters, such as $C_1$ to $C_{22}$ normal or branched alkyl esters of methacrylic acid, including methyl methacrylate, ethyl methacrylate, n-butyl methacrylate, iso-butyl methacrylate, 2-ethylhexyl methacrylate, lauryl methacrylate, stearyl methacrylate, isobornyl methacrylate; acrylate esters such as $C_1$ to $C_{22}$ normal or branched alkyl esters of acrylic acid, including methyl acrylate, ethyl acrylate, n-butyl acrylate, 2-ethylhexyl acrylate; styrene; substituted styrenes such as methyl styrene, α-methyl styrene, or t-butyl styrene; vinyl esters of organic acids, such as vinyl acetate; N-vinyl compounds such as N-vinyl pyrrolidone; acrylamide; methacrylamide; substituted acrylamides such as N-alkyl acrylamides and amine-functional acrylamides including, for example, dimethylaminopropylacrylamide; substituted methacrylamides; hydroxyalkyl methacrylates such as hydroxyethyl methacrylate; hydroxyalkyl acrylates; dienes such as 1,3-butadiene and isoprene; vinyl ethers; and combinations thereof. The ethylenically unsaturated monomers can also be an acid containing monomers or a functional monomer such as maleic acid, maleic anhydride, fumaric acid, a-methylene glutaric acid, itaconic acid, itaconic anhydride, citraconic acid, mesaconic acid, cyclohexenedicarboxylic acid, 2-acrylamido-2-methylpropanesulfonic acid, monoacryloxyethyl phosphate, and water-soluble salts thereof.

Polyurethanes and polyureas of this invention may be prepared by conventional polymerization methods well known to those skilled in the art such as, for example, using methods disclosed in European Patent 0 859 804 and European Patent 0 619 111. They are produced by reacting: 1) two or more diols such as, for example, polyoxyalkylene diols such as polyethylene glycols and polypropylene glycols of various molecular weights; polyesterdiols such as polyesterdiol Fomrez 8066-72 (available from Crompton); small molecular diols such as methyl 1,3-propanediol, neopentyl glycol; diamine for polyureas with 2) one or more diisocyanates such as, for example, isophorone diisocyanate, methylene-bis(4-cyclohexylisocyanate), toluene diisocyanate, hexamethylene diisocyanate, 4,4'-methylenebis(phenyl diisocyanate), and, optionally, 3) an acid containing diol to impart hydrophilicity to the polymer such as, for example, 2,2-di(hydroxylmethyl) propionic acid.

Polyesters and polyesteramides of this invention may be prepared by conventional polymerization methods well known to those skilled in the art such as those disclosed in U.S. Pat. No. 6,136,884. They are produced by reacting: 1) two or more diols such as, for example, polyoxyalkylene diols such as polyethylene glycols and polypropylene glycols of various molecular weights; polyesterdiols such as polyesterdiol Fomrez 8066-72 (available from Crompton); small molecular diols such as methyl 1,3-propanediol, neopentyl glycol, 1,4-cyclohexanedimethanol; diamine for polyesteramides; with 2) one or more dicarboxylic acids such as isophathalic acid; and, optionally, 3) a sulfonate diacid to impart hydrophilicity to the polymer such as, for example, 5-sulfoisophathalic acid, sodium salt.

The term "(meth)acrylate" means methacrylic or acrylic acid, their salts and esters, methacrylamide, and acrylamide. Preferably, (meth)acrylic esters are linear or branched chain $C_1$-$C_{22}$ alkyl esters. The term "(meth)acrylic acid" means methacrylic acid or acrylic acid. Preferred (meth)acrylate monomers useful in the polymers of the present invention include methyl acrylate, ethyl acrylate, butyl acrylate, methacrylic acid, hydroxyethylmethacrylate, and methyl methacrylate. Other acrylate related monomers are also useful in the polymers of this invention such as, for example, dimethylaminopropylacrylamide. Dicarboxylic acid monomers useful in the polymers of the present invention include, for example, maleic acid, maleic anhydride, fumaric acid, α-methylene glutaric acid, itaconic acid, itaconic anhydride, citraconic acid, mesaconic acid, crotonic acid, cyclohexenedicarboxylic acid, and water-soluble salts thereof.

The high Tg polymer and the low Tg polymer may be prepared as individual polymers using methods such as, for example, those disclosed in European Patent No. 0 985 405 and mixed together to form the composition of this invention. The polymer blend may also be prepared using a multistage polymerization process such as, for example, those disclosed in U.S. Pat. Nos. 4,445,402 and 6,136,884 to produce a blend in situ or an interpenetrating polymer network using methods such as, for example, that described in European. Patent 0 392 767.

The polymers utilized in the polymer composition of this invention should be compatible in hair styling compositions. To test the compatibility of the polymers, the polymers are first dissolved in a mutual solvent to form a solution of the polymers. The solvent is evaporated leaving a film. Incompatible polymers will form a cloudy film with poor mechanical properties, including low tensile storage modulus at higher temperatures. A characteristic of the polymer compositions of this invention is that when dried, they form flexible, tough films characterized as having a tensile storage modulus, E', at 20° C. of from $1\times10^{10}$ Pascal ("Pa") to $1\times10^8$ Pa and an E' at 70° C. of from $1\times10^9$ Pa to $1\times10^6$ Pa, more preferably $1\times10^9$ Pa to $1\times10^7$ Pa, most preferably $5\times10^8$ Pa to $1\times10^7$ Pa.

The molecular weights of the polymers may vary depending upon the polymer chemistry and the demands of the application. For example, molecular weights of polymers used in gels will generally be higher than those used in sprays.

The polymers in the polymer compositions of this invention are preferably added to hair styling compositions to provide a total concentration of from 0.1 to 15%, more preferably from 1 to 10%, and most preferably from 4 to 7%, based on the total weight of the hair styling composition. Typically gels will have a polymer concentration of from 0.5% to 4%, preferably 1% to 2% and sprays will have a concentration of from 4% to 7%. Hair styling compositions comprising the polymer compositions of this inventions are applied to wet or dry hair by spraying or by rubbing onto the hair manually. The treated hair is then mechanically fixed in the desired configuration using, for example, any of a variety of hair styling implements such as, for example, combs, brushes, rollers, or curlers. When applied to wet hair, after application the hair may be dried using ambient air, electric, or hot air drying, before, during, or after styling. Thus, another embodiment of this invention is a method for styling hair comprising the steps of:

a) applying to the hair an effective styling amount of a composition comprising:

i) a first polymer or polymer mixture with a glass transition temperature from 30° C. to 250° C.;

ii) a second polymer or polymer mixture with a glass transition temperature from minus 20° C. to 35° C.; and iii) one or more cosmetically acceptable solvents;

wherein the difference in the glass transition temperatures of the first polymer or polymer mixture and the second polymer or polymer mixture is 10° C. or more; and wherein when the first polymer or polymer mixture and the second polymer or polymer mixture are dissolved in a cosmetically acceptable solvent and then dried to form a film, the film has a tensile storage modulus at 20° C. of from $1\times10^{10}$ Pascal to $1\times10^{8}$ Pascal and a storage modulus at 70° C. of from $1\times10^{9}$ Pascal to $1\times10^{6}$ Pascal; and b) fixing the hair in a desired configuration.

In some cases steps a) and b) may be reversed to obtain the desired styling result. The term "effective styling amount" means an amount of the composition that will hold the hair in a desired style.

The polymer compositions of this inventions may be prepared by conventional polymerization methods well known to those skilled in the art including, for example, emulsion, solution, bulk, and suspension polymerization. The (meth)acrylic polymers are preferably prepared by emulsion polymerization such as those methods disclosed in U.S. Pat. Nos. 3,245,932, 3,453,245 and 4,196,190.

The polymer compositions that are useful in hair styling compositions are soluble in the hair styling composition "as is" or upon neutralization of some or all of the acid groups contained in the polymer composition. The acidic groups in the polymer mixture of this invention, such as carboxylic acid groups, may be neutralized by conventional techniques with at least one base to dissolve the polymer in the hair styling composition. Bases that will neutralize the polymer mixture may be selected from one or more amines, alkali or alkaline earth metal hydroxides, and ammonium hydroxide. Suitable amine neutralizers include, for example, 2-amino-2-methyl-1,3-propanediol, 2-amino-2-methyl-1-propanol, N,N-dimethyl-2-amino-2-methyl-1-propanol, mono-isopropanolamine, triisopropanolamine, ethanolamine, triethanolamine, cyclohexylamine, and morpholine. Suitable alkali or alkaline earth metal hydroxides include, for example, sodium hydroxide and potassium hydroxide. Preferably, the neutralizer is selected from one or more of 2-amino-2-methyl-1,3-propanediol, 2-amino-2-methyl-1-propanol, N,N-dimethyl-2-amino-2-methyl-1-propanol, potassium hydroxide, triethanolamine and triisopropanolamine.

The minimum amount of neutralizer added to the hair styling composition is that amount needed to provide solubility of the polymer mixture in the hair styling composition and to ensure that the pH or the hair styling composition is cosmetically acceptable. Typically from 5 to 100%, preferably from 10 to 100%, more preferably from 50 to 100%, and most preferably from 75 to 100%, based on molar equivalents, of the acid groups in the hair fixative resins are neutralized.

The polymer compositions, if sprayed, preferably have a viscosity which is compatible with the spray apparatus from which the composition is dispensed. Typically the viscosity will be less than or equal to $15\times10^{-3}$ pascal·seconds (Pa·sec) (15 centipoise) when dissolved in a pump hair styling composition at a polymer concentration of about 5% or less, based on the total weight of the hair styling composition, and less than $25\times10^{-3}$ Pa·sec in an aerosol concentrate.

The polymer compositions of this invention may also be blended with one or more other hair fixative polymers such as, for example, the acrylic polymers described previously, and other soluble hair fixative polymers such as, for example, butyl acrylate/ethyl acrylate/methacrylic acid copolymers, poly(vinyl pyrrolidone)/vinyl acetate copolymers, octylacrylamide/acrylates/butylaminoethyl-methacrylate copolymers, vinylcaprolactam/vinyl-pyrrolidone/dimethylaminoethyl-methacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, and polyesters. Additional hair fixative polymers useful for blending with the polymer compositions of this invention include, for example (by INCI name), PVP/VA copolymer, ethey ester of PVM/MA copolymer, butyl ester of PVM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyacrylates copolymer, acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, PVP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, Preferably, the hair fixative polymers are the acrylic hair fixative polymers described previously.

In addition to the polymer compositions of this invention, hair styling compositions may contain any other ingredient used in cosmetics such as, for example, perfumes, dyestuffs which can color the hair styling composition itself or hair fibers, preservatives, sequestering agents, thickeners, silicones, softeners, foam synergistic agents, foam stabilizers, sun filters, peptizing agents, conditioning agents, shine agents, proteins, herbals, botanicals, neutralizers, plasticizers, and anionic, non-ionic, cationic, or amphoteric surfactants, or mixtures thereof.

One or more surfactants may be added to the hair styling composition, typically to reduce the surface tension of the composition. When surfactants are present in the hair styling composition, they are preferably present at a concentration of from 0.001 to 1%, based on the total weight of the composition.

One or more plasticizers may be added to the hair styling composition of the present invention. When plasticizers are present in the hair styling composition, they are preferably present at a concentration of from 0.001 to 1%, based on the total weight of the composition. The plasticizers that may be used in the hair styling composition include, for example, dimethicone copolyol, dimethicone, phenyltrimethicones, trialkylcitrates, and others that are known and typically used in the art.

Hair styling compositions comprising the polymer compositions of this invention are preferably water, or alcohol, or water/alcohol mixture based compositions. However, the compositions can comprise any other cosmetically acceptable solvents such as, for example, monoalcohols such as, for example, alcohols containing from 1 to 8 carbon atoms including ethanol, isopropanol, benzyl alcohol, and phenylethyl alcohol; polyalcohols such as, for example, alkylene glycols such as glycerine, ethylene glycol and propylene glycol; glycol ethers such as mono-, di-, and tri-ethylene glycol monoalkyl ethers; ketones, ethers, esters; and mixtures thereof. Water and other solvents may be used alone or in mixtures. Such solvents may be present in proportions of up to 99.9 percent of the hair styling composition.

In a hair styling composition using an aerosol spray, one or more propellants are used. Preferably the propellants are used at a total concentration of from 10 to 70%, more preferably from 30 to 60%, based on the total weight of the hair styling composition. Suitable propellants include, for example, hydrocarbons such as n-butane, isobutane, and pentane; ethers such as dimethyl ether; chlorofluorocarbons such as difluoroethane, chlorodifluoroethane, chlorodifluoromethane, and other chlorofluorocarbons; and mixtures thereof. Preferred propellants are selected from one or more of dimethyl ether, 1,1-difluoroethane, n-butane and isobutane. These propellants are available commercially.

Preservatives may be used in the hair styling composition including, for example, one or more of isothiazolones, iodopropynylbutyl carbamate, benzyl alcohol, imidazolidinylurea and alkyl parabens.

One or more thickeners may be desirable in a hair styling composition that is applied to the hair in the form of a styling gel. Suitable thickeners include, for example, polycarboxylic acid thickeners such as acrylates/steareth-20 methacrylate copolymer, acrylates copolymer, or acrylates $C_{10-30}$ alkyl acrylate crosspolymer; carbomers, hydroxyethyl cellulose, PVM/MA decadiene crosspolymer, steareth-10 allyl ether/acrylate copolymer, hydrophobically modified polyethoxylated urethane thickeners, starch-based thickeners, and polyamide thickeners. The thickeners, when used, preferably are present at a total concentration of from 0.001 to 5%, based on the total weight of the composition.

Other additives, such as those commonly used by those skilled in the art, may be added to the hair styling composition. The other additives used in the hair styling composition will depend upon the type of hair styling composition desired. Other additives include, for example, one or more of; moisturizers (such as glycerine, hydrolyzed silk protein, and hydrolyzed wheat protein); conditioning agents such as panthenol; conditioning agents (U.S. Pat. No. 5,164,177 may be consulted for further general and specific details on suitable conditioning agents); emulsifiers; antistatic aids; extracts; proteins; vitamins; colorants; UV protectors; fragrances, and corrosion inhibitors. Such other additives typically comprise from 0.005 to 5%, and more preferably from 0.01 to 1%, of the hair styling composition.

Additives, including surfactants, solvents, other preservatives, and thickeners, that may be suitable in the hair styling compositions may be found in the International Cosmetic Ingredients Dictionary, 9th Edition, 2002, published by the Cosmetics Toiletries Fragrances Association (CFTA), Washington D.C.

EXAMPLES

Blend Preparation

Hair fixative compositions were prepared by combining each material as detailed in Tables 3-5 and neutralizing to pH 7.5 using aminomethyl propanol. The polymer quantities in Tables 3-5 are listed as weight percent active solids. The polymers used in the blends are described in Tables 1 and 2

Hair Stiffness and Stiffness Retention Determination

Hair tresses (European Brown Virgin Hair, obtained from DeMeo Brothers, New York) prior to curling were on average 8 inches long and weighed 3.5±0.1 grams. They were washed in mild shampoo before using and curled wet onto a 22 millimeter ("mm")×70 mm curler and held in place with a bobby pin. The curled tresses were allowed to air dry on a lab bench overnight.

The curled tresses were uniformly sprayed twice in the front and twice on the back from a distance of 20.3 centimeters ("cm") with the hair spray formulations described in Table 6. The spray device delivered 190 µL (microliters) of formulation with each compression. The spray device product was "Euromist Classic", manufactured by SequistPerfect, Cary, Ill. The curled, treated tresses were dried for 1 hour in a controlled environment at 22.5° C. and 55% relative humidity. The curler was removed carefully without uncurling the tress. The curled tress was placed in a miniature tensile tester, model MTT160 instrument (Dia-Stron Limited, Unit 9 Focus 303 Business Centre, Andover, Hampshire SP10 5NY UK, or 390 Reed Road, Broomall, Pa. 19008, USA) and the work to compress the curl to 50% of its initial diameter was measured. The compression was repeated 5 times for each tress. Measurements were made at about 22.5° C. and 55% relative humidity. The percent stiffness retention was determined by the following equation:

$$\% \text{ stiffness retention} = (w_5/w_i) \times 100,$$

where $w_i$ is the work of the first compression and $w_5$ is the work needed to compress the curl on the fifth consecutive compression. In this test, good stiffness retention is taken to be a measure of good durability on the hair. Satisfactory stiffness retention values are greater than 80%, preferably greater than 85%, and more preferably greater than 90%.

Film Preparation and Evaluation

Dried film samples were prepared by drying approximately 16 g (grams) of each hair spray composition in Tables 3-5 in a flat bottom PTFE (polytetrafluoroethylene) evaporating dish with a diameter of 63 mm. The films were dried at room temperature for 48 hours, were removed from the dishes, and conditioned at about 22° C. and 55% relative humidity for at least 2 hours before evaluation. The evaluation standard is as follows:

| Rating | Flexibility | Toughness | Tackiness |
| --- | --- | --- | --- |
| 1 | brittle | very soft, flowable | very tacky |
| 2 | slightly brittle | soft | slightly tacky |
| 3 | slightly flexible | slightly tough | very slightly tacky |
| 4 | flexible | tough | no tack |

Modulus Measurements

The rheological properties of the dried films prepared as above were determined using the Rheometric Scientific's Dynamic Mechanical Thermal Analyzer (DMTA) model Mark IV. The tests were carried out in tension mode using the film fixtures. Prior to performing the experiments the following calibrations to the instrument were applied: electronics, dynamic mode, position, and force. These calibrations were carried out according to Rheometric Scientific guidelines. The viscoelastic properties of the materials were investigated by carrying out a temperature sweep at 3° C./min, and maintaining constant the frequency of oscillation at 1 Hz. The amplitude of oscillation was typically 0.005%, and within the linear viscoelastic regime of the materials (the linear viscoelastic regime is defined as the range of strains where the dynamic moduli remain constant, at a given frequency).

Tg Measurement

Glass transition temperatures (Tg) were measured using TA instruments model 2920 Differential Scanning Calorimeter either with conventional (20° C./min ramp rate) or modulated temperature ramp test method.

Molecular weight measurement

Molecular weights of polymers can be measured according to the following procedure either with THF or DMF as an eluting solvent:
1) THF: the measurement was performed on a system that contains an Agilent 1100 series HPLC pump, two coupled Polymer Lab 20 um mixed bed columns, Water 410 RI detector at 35° C.
2) DMF: the measurement was performed with Waters 150 C gel permeation chromatography at 60° C.

The following abbreviations used in the tables and example:

| | |
|---|---|
| BA = | Butyl Acrylate |
| EA = | Ethyl Acrylate |
| HEMA = | Hydroxyethyl Methacrylate |
| MAA = | Methacrylic Acid |
| VA = | Vinyl Acetate |
| PVP = | Poly Vinyl Pyrrolidone |
| DMAPA = | Dimethylaminopropylacrylamide |
| PVM = | poly Vinyl methyl ether |
| MA = | Methyl Acrylate |
| CHDM = | 1,4-Cyclohexane dimethanol |
| SIP = | Sodiosulfoisophthalic acid |
| HDI | Hexamethylene diisocyanate |

Please Check These Abbreviations

The following High Tg polymers were utilized in the compositions evaluated in the examples:

TABLE 1

| No. | INCI Name | Trade Name | Manuf. | Tg° C. |
|---|---|---|---|---|
| 1 | Acrylates/C1-2 Succinates/ Hydroxy Acrylates Copolymer | Allianz LT-120 | 1 | 90 |
| 2 | Acrylates/Hydroxyesters Acrylates Copolymer | Acudyne 258 | 1 | 80 |
| 3 | Octylacrylamide/Acrylates/ Butylaminoethyl Methacrylate Copolymer | Balance 47 | 2 | 130 |
| 4 | Octylacrylamide/Acrylates/ Butylaminoethyl Methacrylate Copolymer | Amphomer LV-71 | 2 | 130 |
| 5 | VA/Crotonates/Vinyl Neodecanoate Copolymer | Resyn 28-2930 | 2 | 53 |

TABLE 1-continued

| No. | INCI Name | Trade Name | Manuf. | Tg° C. |
|---|---|---|---|---|
| 6 | acrylates copolymer | Balance 0/55 | 2 | 49 |
| 7 | sodium polystyrene sulfonate | Flexan 130 | 2 | 112 |
| 8 | acrylates copolymer | Luvimer 36D | 3 | 95 |
| 9 | Polyurethane-1 | Luviset PUR | 3 | 74.5/ 120 |
| 10 | PVP/Vinylcaprolactam/DMAPA Acrylates Copolymer | Aquaflex SF-40 | 4 | 138 |
| 11 | Isobutylene/Ethylmaleimide/ Hydroxyethylmaleimide Copolymer | Aquaflex FX-64 | 4 | 121 |
| 12 | Vinyl Caprolactam/PVP/ Dimethylaminoethyl Methacrylate Copolymer | Gaffix VC-713 | 4 | 85 |
| 13 | Butyl Ester of PVM/MA Copolymer | Gantrez A-425 | 4 | |
| 14 | PVP | PVP K-30 | 4 | |
| 15 | PVP/VA | PVP/VA W635 | 4 | 98 |
| 16 | Diglycol/CHDM/isophthalates/ SIP copolymer | AQ-48 Ultra | 5 | 48 |

Manufacturers:
1 = Rohm and Haas Company
2 = National Starch and Chemical Company
3 = BASF Corporation
4 = International Specialty Products
5 = Eastman Chemical Company
Trade Names are trademarks of the manufacturers.

The following low Tg polymers were utilized in the compositions evaluated in the examples:

TABLE 2

| No. | Composition | Tg |
|---|---|---|
| a | 20 BA/55 EA/15 HEMA/10 MAA | 6.4 |
| b | 20 BA/50 EA/15 HEMA/15 MAA | 25 |
| c | 20 BA/40 EA/30 HEMA/10 MAA | 26 |
| d | 20 BA/35 EA/30 HEMA/15 MAA | 34 |
| e | 20 BA/50 EA/20 HEMA/10 MAA | 13 |
| f | 20 BA/55 EA/10 HEMA/15 MAA | 18 |
| g | 0.24 Polyesterdiol(IPA-Adipic-Hexandiol Mw 1K)/0.03 PEG 1500/0.66 DMPA/1 HDI | 12 |

Evaluation of the hair styling composition blends provided the following film property results for blends made using a multi stage polymerization process:

TABLE 3

| | High Tg polymer | | Low Tg polymer | | Solvents | | Film Properties | | |
|---|---|---|---|---|---|---|---|---|---|
| Ex. No | Polymer % | No. | Polymer % | No. | Deionized water % | Ethanol % | Flexibility | Toughness | Tackiness |
| 1a | 2.5 | 1 | 2.5 | a | 40 | 55 | 4 | 4 | 4 |
| 2a | 2 | 1 | 3 | a | 40 | 55 | 4 | 4 | 4 |
| 3a | 2.5 | 1 | 2.5 | d | 40 | 55 | 3 | 4 | 4 |
| 4a | 2 | 2 | 3 | a | 40 | 55 | 4 | 3 | 4 |
| 5a | 2 | 2 | 3 | b | 40 | 55 | 4 | 4 | 4 |
| 6a | 1.75 | 2 | 3.25 | b | 40 | 55 | 4 | 3 | 4 |
| 7a | 2.5 | 2 | 2.5 | a | 40 | 55 | 4 | 4 | 4 |

Evaluation of the hair styling composition blends provided the following film property results for blends using mixtures of single stage polymers:

TABLE 4

| Ex. No | High Tg polymer % | Polymer No. | Low Tg polymer % | Polymer No. | Solvents Deionized water % | Ethanol % | Film Properties Flexibility | Toughness | Tackiness |
|---|---|---|---|---|---|---|---|---|---|
| 1b | 2 | 1 | 3 | a | 40 | 55 | 4 | 3 | 3 |
| 2b | 2.5 | 1 | 2.5 | a | 40 | 55 | 3 | 4 | 4 |
| 3b | 2 | 2 | 3 | a | 40 | 55 | 4 | 3 | 4 |
| 4b | 2 | 2 | 3 | b | 40 | 55 | 4 | 4 | 4 |
| 5b | 2 | 2 | 3 | c | 40 | 55 | 4 | 4 | 4 |
| 6b | 2 | 2 | 3 | d | 40 | 55 | 3 | 4 | 4 |
| 7b | 2 | 2 | 3 | e | 40 | 55 | 4 | 4 | 4 |
| 8b | 2 | 2 | 3 | f | 40 | 55 | 4 | 4 | 4 |
| 9b | 2 | 4 | 3 | b | 40 | 55 | 4 | 4 | 4 |
| 10b | 2 | 6 | 3 | b | 40 | 55 | 4 | 3 | 4 |
| 11b | 2 | 10 | 3 | b | 15 | 80 | 3 | 3 | 4 |
| 12b | 2 | 11 | 3 | b | 40 | 55 | 4 | 3 | 3 |
| 13b | 2 | 12 | 3 | b | 15 | 80 | 4 | 4 | 4 |
| 14b | 2 | 8 | 3 | b | 40 | 55 | 4 | 4 | 4 |
| 15b | 2 | 9 | 3 | g | 40 | 55 | 4 | 4 | 4 |
| 16b | 2 | 14 | 3 | b | 40 | 55 | 4 | 3 | 4 |
| 17b | 2 | 15 | 3 | b | 40 | 55 | 4 | 3 | 3 |
| 18b | 2.25 | 13 | 2.75 | b | 15 | 80 | 4 | 3 | 3 |
| 19b | 2 | 3 | 3 | g | 40 | 55 | 4 | 4 | 4 |
| 20b | 2.5 | 1 | 2.5 | g | 40 | 55 | 4 | 4 | 4 |

Evaluation of comparative hair styling compositions incorporating polymer blends which did not posses the film properties of this invention, that is, they were not compatible, provided the following film property results:

TABLE 5

| Ex. No | High Tg polymer % | Polymer No. | Low Tg polymer % | Polymer No. | Solvents Deionized water % | Ethanol % | Film Properties Flexibility | Toughness | Tackiness |
|---|---|---|---|---|---|---|---|---|---|
| 1a | 3.25 | 16 | 1.75 | a | 40 | 55 | 4 | 2 | 3 |
| 2c | 2.5 | 9 | 2.5 | b | 40 | 55 | 4 | 2 | 3 |
| 3c | 2.5 | 5 | 2.5 | b | 40 | 55 | 4 | 2 | 3 |
| 4c | 1.75 | 7 | 2.25 | b | 40 | 55 | 4 | 2 | 2 |

Evaluation of comparative hair styling compositions incorporating only single polymers rather than the polymer blends of this invention provided the following film property results:

TABLE 6

| Example | Polymer % | Polymer No. | Solvents Deionized water % | Ethanol % | Film Properties Flexibility | Toughness | Tackiness |
|---|---|---|---|---|---|---|---|
| High Tg polymers | | | | | | | |
| 1d | 5 | 1 | 40 | 55 | 1 | 4 | 4 |
| 2d | 5 | 2 | 40 | 55 | 1 | 4 | 4 |
| 3d | 5 | 3 | 40 | 55 | 1 | 4 | 4 |
| 4d | 5 | 4 | 40 | 55 | 1 | 4 | 4 |
| 5d* | 5 | 5 | 40 | 55 | 1 | 4 | 4 |

TABLE 6-continued

| Example | Polymer % | Polymer No. | Solvents Deionized water % | Ethanol % | Film Properties Flexibility | Toughness | Tackiness |
|---|---|---|---|---|---|---|---|
| 6d* | 5 | 6 | 40 | 55 | 1 | 4 | 4 |
| 7d | 5 | 7 | 40 | 55 | 3 | 3 | 4 |
| 8d | 5 | 8 | 40 | 55 | 1 | 4 | 4 |
| 9d | 5 | 9 | 40 | 55 | 2 | 4 | 4 |
| 10d | 5 | 10 | 15 | 80 | 2 | 4 | 4 |
| 11d | 5 | 11 | 40 | 55 | 1 | 4 | 4 |
| 12d | 5 | 12 | 15 | 80 | 1 | 4 | 4 |
| 13d | 5 | 13 | 15 | 80 | 1 | 4 | 4 |
| 14d* | 5 | 14 | 40 | 55 | 1 | 4 | 4 |
| 15d* | 5 | 15 | 40 | 55 | 1 | 4 | 4 |
| Low Tg polymers | | | | | | | |
| 16d | 5 | a | 40 | 55 | 4 | 1 | 1 |
| 17d | 5 | d | 40 | 55 | 3 | 2 | 2 |
| 18d | 5 | g | 40 | 55 | 4 | 1 | 1 |

*= Evaluated at 40% relative humidity because of sensitivity of the film to water.

These data indicate that the blends of this invention provide films with excellent flexibility and toughness and very low tackiness when compared with the single polymer compositions and compositions of incompatible polymer blends.

Certain of the polymer blends were evaluated for hair stiffness and stiffness retention with the following results:

TABLE 7

| Example No. | Polymers | Relative Stiffness | % Stiffness Retention |
|---|---|---|---|
| 1a | 1, a | 1.33 | 91% |
| 4b | 2, b | 1.26 | 89% |
| 5a | 2, a | 1.04 | 89% |
| 2a | 1, a | 0.98 | 91% |
| 7a | 2, b | 0.90 | 88% |
| 3b | 2, a | 0.73 | 87% |
| 6a | 2, b | 0.69 | 92% |

| Comparison Examples | Polymer | Relative Stiffness | % Stiffness Retention |
|---|---|---|---|
| stiff feel 1 | 1d | 1.07 | 62% |
| soft feel 1 | 2d | 0.98 | 80% |
| | 4d | 1.18 | 55% |
| | 8d | 0.72 | 81% |

These data indicate that the polymer blend compositions of this invention provide excellent stiffness retention on hair when compared with single polymers and commercial products and that the performance on hair is consistent with film properties found in Tables 3, 4, and 6.

We claim:

1. A composition comprising:
a) a first polymer or polymer mixture with a glass transition temperature ("Tg") from 75° C. to 130° C.;
b) a second polymer or polymer mixture with a Tg from 20° C. to 35° C.; and
c) one or more cosmetically acceptable solvents;
wherein when the first polymer or polymer mixture and the second polymer or polymer mixture are dissolved together in a cosmetically acceptable solvent, which may be the same as or different than the solvent in c), and then dried to form a film, the film has a tensile storage modulus at 20° C. of from $1\times10^{10}$ Pascal to $1\times10^{8}$ Pascal and a storage modulus at 70° C. of from $1\times10^{9}$ Pascal to $1\times10^{6}$ Pascal; and
wherein the first polymer and the second polymer are independently selected from block, graft, and branched homopolymers and copolymers derived from one or more monomers selected from methacrylic acid; acrylic acid; methacrylate esters, acrylate esters, styrene, substituted styrenes, vinyl esters of organic acids, N-vinyl compounds, acrylamide; methacrylamide; substituted acrylamides, amine-functional acrylamides, substituted methacrylamides; hydroxyalkyl methacrylates, hydroxyalkyl acrylates, dienes, vinyl ethers, acid containing monomers; and functional monomers selected from maleic acid, maleic anhydride, fumaric acid, α-methylene glutaric acid, itaconic acid, itaconic anhydride, citraconic acid, mesaconic acid, cyclohexenedicarboxylic acid, 2-acrylamido-2-methylpropanesulfonic acid, monoacryloxyethyl , and water-soluble salts thereof.

2. A hair styling composition comprising:
a) a composition of claim 1; and
b) one or more cosmetically acceptable solvents; and
c) one or more cosmetically acceptable ingredients selected from perfumes, dyostuffs, preservatives, sequestering agents, thickeners, silicones, softeners, foam synergistic agents, foam stabilizers, sun filters, peptizing agents, conditioning agents, shine agents, proteins, herbals, botanicals, neutralizers, plasticizers, and anionic, non-ionic, cationic, or amphoteric surfactants, and mixtures thereof.

* * * * *